(12) United States Patent
Ritter et al.

(10) Patent No.: US 8,162,920 B2
(45) Date of Patent: Apr. 24, 2012

(54) MAGNETIC NAVIGATION OF MEDICAL DEVICES IN MAGNETIC FIELDS

(75) Inventors: Rogers C. Ritter, Charlottesville, VA (US); Raju R. Viswanathan, St. Louis, MO (US); Roger N. Hastings, Maple Grove, MN (US)

(73) Assignee: Stereotaxis, Inc., St. Louis, MO (US)

( * ) Notice: Subject to any disclaimer, the term of this patent is extended or adjusted under 35 U.S.C. 154(b) by 2454 days.

(21) Appl. No.: 10/831,533

(22) Filed: Apr. 23, 2004

(65) Prior Publication Data

US 2004/0260172 A1 Dec. 23, 2004

Related U.S. Application Data

(60) Provisional application No. 60/465,618, filed on Apr. 24, 2003.

(51) Int. Cl.
*A61M 31/00* (2006.01)
*A61M 25/00* (2006.01)
(52) U.S. Cl. .......................... 604/510; 604/528
(58) Field of Classification Search .................. None
See application file for complete search history.

(56) References Cited

U.S. PATENT DOCUMENTS

| | | | | |
|---|---|---|---|---|
| 5,415,633 A | * | 5/1995 | Lazarus et al. | 604/95.05 |
| 5,876,373 A | * | 3/1999 | Giba et al. | 604/95.04 |
| 6,216,026 B1 | | 4/2001 | Kuhn et al. | |
| 6,304,769 B1 | * | 10/2001 | Arenson et al. | 600/424 |
| 6,385,472 B1 | * | 5/2002 | Hall et al. | 600/374 |
| 6,401,723 B1 | | 6/2002 | Garibaldi et al. | |
| 2002/0116034 A1 | * | 8/2002 | Miller et al. | 607/33 |

* cited by examiner

*Primary Examiner* — Nicholas Lucchesi
*Assistant Examiner* — Pritesh Patel
(74) *Attorney, Agent, or Firm* — Harness, Dickey & Pierce, P.L.C.

(57) ABSTRACT

A method of turning a medical device with the assistance of an externally applied magnetic field, in a direction with a component in a plane perpendicular to the direction of the externally applied magnetic field. The method includes applying first torque to the distal end of the medical device by creating magnetic moment at the distal end of the medical device, and applying a second torque to the distal end of the medical device. The second torque may be created by creating a second magnetic moment at the distal end of the device spaced from the first, by using an electrostrictive device, by using a stylette inserted into the device, by using a fluid-driven shaped tube, or otherwise.

28 Claims, 6 Drawing Sheets

MAGNETIC NAVIGATION OF MEDICAL DEVICES IN MAGNETIC FIELDS

CROSS REFERENCE TO RELATED APPLICATION

This application claims priority of prior provisional U.S. Application Ser. No. 60/465,618, filed Apr. 24, 2003, the entire disclosure of which is incorporated herein by reference.

BACKGROUND OF THE INVENTION

This invention relates to the navigation of medical devices in magnetic fields, and in particular to the navigation of medical devices in magnetic fields created by magnetic resonance imaging equipment.

Systems have been developed for navigating medical devices in externally applied static magnetic fields, such as those created by magnetic resonance imaging equipment. Examples of such systems are disclosed in Kuhn, U.S. Pat. No. 6,216,026, Arenson, U.S. Pat. No. 6,304,769, and Hastings et al., U.S. Pat. No. 6,401,723, the disclosures of all of which are incorporated herein by reference. These systems employ a controllable variable magnetic moment in the medical device to orient the magnetic medical device relative to the externally applied magnetic field. One way of creating a controllable variable magnetic moment is with one or more coils in the distal end which can be selectively energized.

Although these prior systems allow effective magnetic navigation in a static magnetic field, magnetic navigation of a medical device in a static magnetic field is constrained by the nature of the interaction between the magnetic moments and the external field. The torque on a dipole moment m in a homogeneous external magnetic field B is given by $\tau = m \times B$. This torque is necessarily perpendicular to the external field B and to the moment m. In navigation it is generally possible to completely vary the direction of m relative to the catheter tip, but in fixed field navigation, such as in an MRI, B cannot be changed. Thus, when the medical device is in a plane that is perpendicular to the external field B, the device cannot be deflected in the plane in which it lies, irrespective of m, because this requires a torque that is parallel to B.

Another difficulty encountered with at least some prior systems for navigating in a static magnetic field of an MRI system is the inductive rf heating of wire leads powering the coils used to change the magnetic moment of the device.

SUMMARY OF THE INVENTION

The present invention provides for the navigation of medical devices in the plane perpendicular to an applied magnetic field, and more specifically turning a medical device with the assistance of an externally applied magnetic field or other means, or a combination thereof, in a direction with a component in a plane perpendicular to the direction of the externally applied magnetic field. Generally the method comprises applying a first torque to the distal end of the medical device by creating a magnetic moment at the distal end of the medical device; and applying a second torque to the distal end of the medical device. This second torque can be applied by creating a second magnetic moment at the distal end of the medical device, spaced from the first. It may also be allowed by mechanically turning the distal end of the medical device, for example by turning the proximal end of the device, by rotating an element anchored to the distal end of the device, inserting a shaped stylette into the medical device, or operating one or more active elements, for example electrostrictive elements or pressure operated elements, for changing the shape of the medical device. In another aspect of various embodiments of this invention, long electrical leads to coils on the distal end of the device are eliminated by providing a fiber optic conduit to a photovoltaic cell in the distal end of the medical device, which powers one or more coils in the distal end of the device.

Thus some embodiments of the method and apparatus of this invention allow a medical device being navigated in a static magnetic field to be turned in a direction in a plane perpendicular to the applied magnetic field. Other embodiments of the method and apparatus of this invention allow apparatus for changing the magnetic moment of the distal end of a medical device without the need for electrical leads extending the length of the device to the distal end. These and other features and advantages will be in part apparent, and in part pointed out hereinafter.

BRIEF DESCRIPTION OF THE DRAWINGS

Corresponding reference numerals indicate corresponding parts throughout the several views of the invention.

DETAILED DESCRIPTION OF THE PREFERRED EMBODIMENT

The present invention provides a method for navigating a medical device in an operating region in a subject's body to which a static magnetic field is applied. As used herein a medical device means any medical device that is navigated in the body, including but not limited to guide wires, catheters, endoscopes, etc. The static magnetic field can be applied with a source magnet that is part of a dedicated magnetic navigation system, or the magnetic field can be applied with a magnet from a magnetic resonance imaging system.

Figure 1:
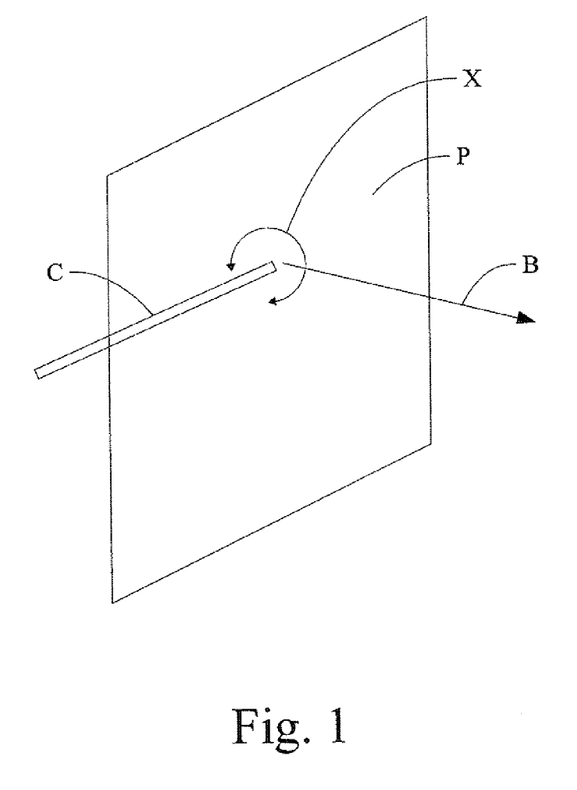
FIG. 1 is a schematic view of a medical device C being navigated in a static applied magnetic field B, lying in a plane P perpendicular to the applied magnetic field.
Figure 2:
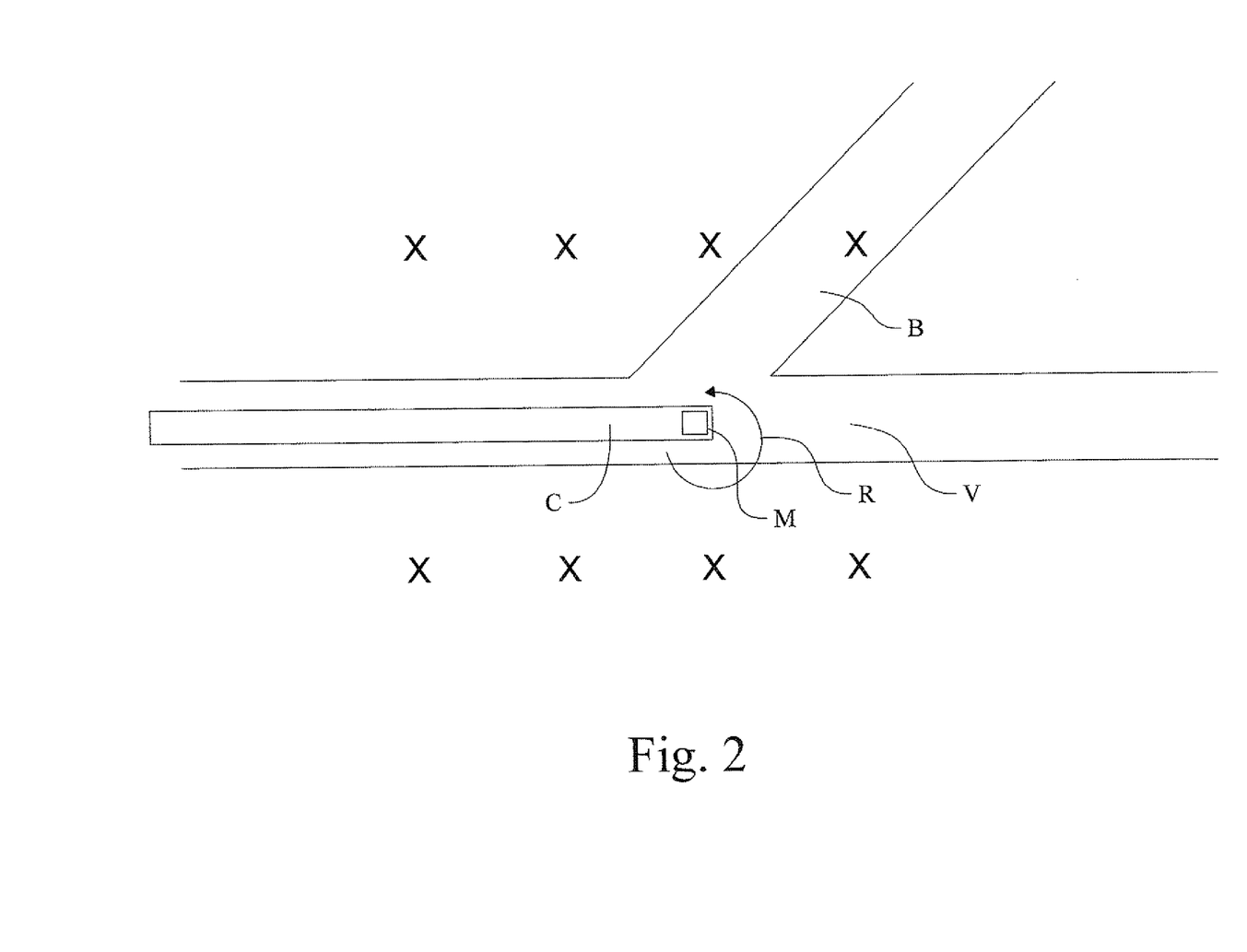
FIG. 2 is a schematic view of a medical device C in a vessel V that lies in a plane perpendicular to the applied magnetic field.

As shown in FIG. 1, when a medical device C lies in a plane P perpendicular to the direction of the applied magnetic field B, it is not possible to move the medical device in the direction indicated by arrow X in the plane P purely by changing the magnetic moment at the distal tip of the medical device. Moreover, it is not possible to move in any arbitrary direction having a component in the plane P purely by changing the moment m. The problem of being unable to navigate in the "forbidden" plane is illustrated in more detail in FIG. 2, where the device C lies an a vessel V and it is desired to turn the device C into a branch D, with both V and C in the plane of the page, which is perpendicular to the field B. As shown in the Figure, the magnetic field direction B is into the paper, as represented by the X's. Thus the turn in direction R is in the plane perpendicular to the magnetic field direction, and cannot be accomplished simply by changing the magnetic moment at the distal end of the device C. Indeed, the magnetic moment interacting with the external magnetic field generally causes the device tip to move out of the plane P defined by V and D. Means to accomplish effective turns of the tip within the plane P require that the tip be moved, however slightly, back into the plane, at which point there will be at least a small component of the bent tip that is along the field direction. The requisite change in m and tip orientation or displacement can then be calculated (by computer. It is part of the object of this invention to have computer optimization of a succession of such small turn combinations so that the complete turn is made optimally for the given geometry. The degree of "adverse lever arm" in using the combination motion depends on the daughter vessel size and on the closeness of the "parent-daughter" plane to the forbidden plane.

Figure 3:
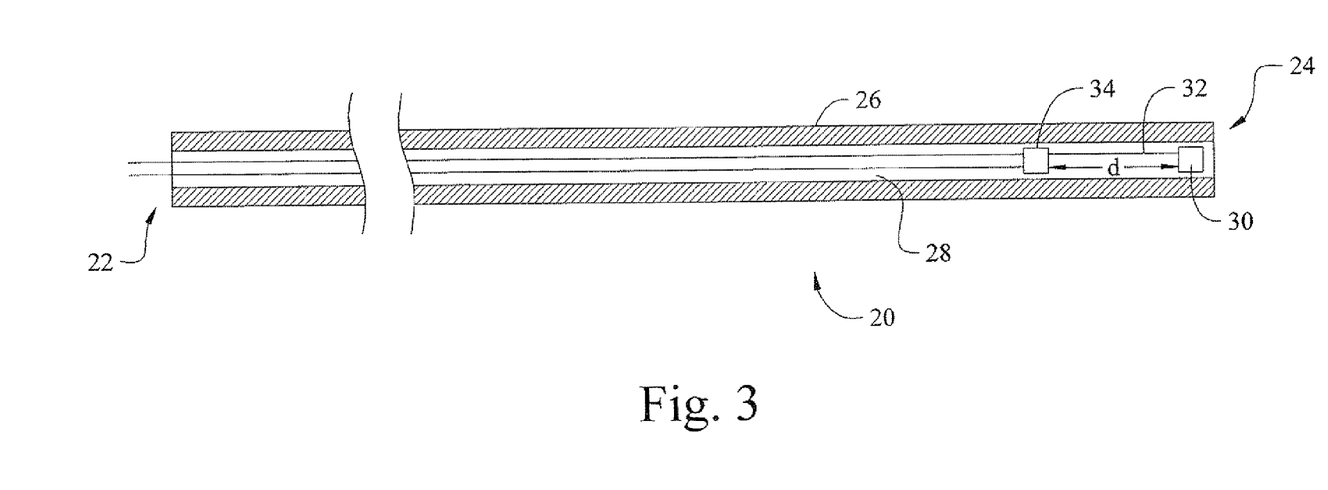
FIG. 3 is a longitudinal cross-sectional view of a first embodiment of a medical device constructed according to the principles of this invention.

A first embodiment of a medical device for navigation in a static magnetic field constructed in accordance with the principles of this invention is indicated generally as 20 in FIG. 3. As shown in FIG. 3, the device 20 is preferably an elongate device having a proximal end 22, a distal end 24, and comprising a generally tubular sidewall 26 with a lumen 28 extending therethrough. The distal end 24 of the medical device 20 preferably includes at least one element 30 for selectively creating a magnetic moment at the distal end of the medical device to orient the distal end of the medical device relative to a static magnetic field applied to the operating region in which the device 20 is being navigated by an external source magnet or magnets. The element 30 may be any of a variety of elements for selectively creating a magnetic moment, but in this preferred embodiment the element 30 comprises at least one electromagnetic coil, and more preferably at least three mutually perpendicular coils. These coils can be arranged on a cubic substrate or simply embedded in the wall of the medical device. The coils can be powered via leads 32, which preferably comprise a pair of leads for separately powering each coil.

The distal end 24 of the medical device 20 preferably includes a second element 34, spaced a distance d from first element 30, for selectively creating a second magnetic moment at the distal end of the medical device 20 to orient the distal end of the medical device relative to a static magnetic field applied to the operating region by the external source magnet or magnets. The element many be any of a variety of elements for selectively creating a magnetic moment, but in this preferred embodiment the element comprises electromagnetic coils, and in particular an electromagnetic coil unit. The coil unit preferably comprises at least three mutually perpendicular coils. These coils can be arranged on a cubic substrate or simply embedded in the wall of the medical device. The coils can be powered via leads 36, which preferably comprise a pair of leads for separately powering each coil. The leads 32 and 36 can either extend through the lumen 28 as shown, extend through a separate lumen (not shown), or be embedded in the wall 26.

The distance d between the elements 30 and 34 is preferably sufficient, given the properties of the medical device, to allow the device to flex between the elements.

The two elements 30 and 34 allow the distal end portion 24 of the medical device 20 to be turned out of the plane perpendicular to the field B, and then turned in the desired direction. The operation of the elements 30 and 34 can be controlled by computer to optimize the efficiency of the turn according to the physical properties of the device (the wall stiffness and the spacing d) and the particular turn that is desired. The turn with component in the forbidden plane is possible with this device because the two moments 30 and 34 created magnetically can react so as to create a mechanical torque between them, which is not subject to the limit of the torque on the magnetic moments themselves. This can be seen from the fact that different torques out of the forbidden plane, when coupled by a flexible mechanical member, can be arranged to have appropriate out-of-plane moments cancel mechanically, so that the complete device can have a turning component in the plane.

Let L be the supported length of device (this depends on the particular medical application) where the device freely extends (measured back from the distal tip). As before, let d be the spacing between the elements 30 and 34. Let E be the Young's modulus of the material of the device and I its bending moment of area. Suppose that the magnetic moment of magnitude m produced by the most distal element 30 causes the device tip to move out of the plane P shown in FIG. 1 by an amount z. Then in order to move the tip back into this plane, the second element 34 is preferably controlled so as to produce a magnetic moment whose magnitude is $m_1 = \beta m(1 + \alpha)$, where $\alpha = (EI/(L-d))(d/L)(z/L)$ and $\beta$ is a number in the range $\frac{1}{5} < \beta < 5$.

It is desirable to know the orientation of the elements 30 and 34 prior to energizing its coils. This can be conveniently done by moving the distal end of the medical device, and using the coils comprising the elements 30 and 34 to measure the static field B and thereby determine their orientation relative to the know orientation of the field B. Another method to determine the orientation is to place a series of MR-visible markers along the device in known orientations relative to one or more of the elements 30 and 34, and to extract the device orientation from appropriate image processing.

Figure 4:
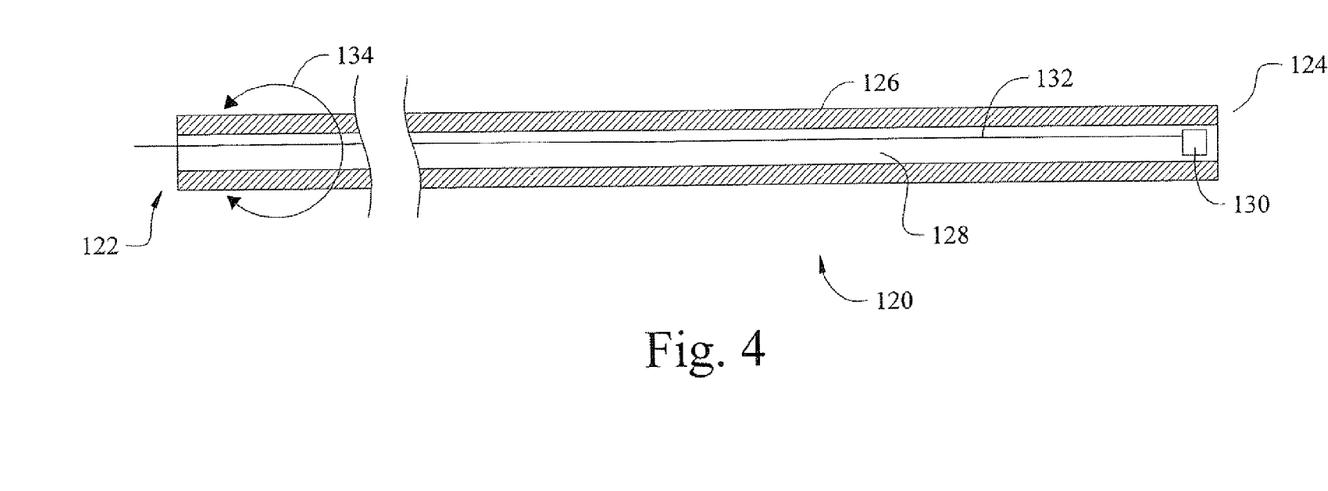
FIG. 4 is a longitudinal cross-sectional view of a second embodiment of a medical device constructed according to the principles of this invention.

A second embodiment of a medical device for navigation in a static magnetic field constructed in accordance with the principles of this invention is indicated generally as 120 in FIG. 4. As shown in FIG. 4, the device 120 is preferably an elongate device having a proximal end 122, a distal end 124, and comprising a generally tubular sidewall 126 with a lumen 128 extending therethrough. The distal end 124 of the medical device 120 preferably includes at least one element 130 for selectively creating a magnetic moment at the distal end of the medical device to orient the distal end of the medical device relative to a static magnetic field applied to the operating region in which the device 120 is being navigated by an external source magnet or magnets. The element 130 may be any of a variety of elements for selectively creating a magnetic moment, but in this preferred embodiment the element 130 comprises at least one electromagnetic coil, and more preferably at least three mutually perpendicular coils. These coils can be arranged on a cubic substrate or simply embedded in the wall of the medical device. The coils can be powered via leads 132, which preferably comprise a pair of leads for separately powering each coil. The leads 232 can either extend through the lumen 228 as shown, extend through a separate lumen (not shown), or be embedded in the wall 226.

In operation, the element 130 is powered via leads 132 to turn the distal end 124 of the medical device 120 out of the "forbidden" plane perpendicular to the direction of the applied magnetic field. The proximal end 122 of the medical device 120 is then rotated as indicated by arrow 134 (about the axis of 120) to turn the distal end 124 of the device in the desired direction. This rotation can be either manually performed or implemented and driven by computer control. The operation of the element 130 can be controlled by computer. It is desirable to know the orientation of the element 130 prior to energizing its coils. This can be conveniently done by moving the distal end of the medical device, and using the coils comprising the element 130 to measure the static field B and thereby determine their orientation relative to the know orientation of the field B; an alternate method for determination of orientation would be based on incorporating MR-visible markers in the device and performing appropriate image processing.

Figure 5:
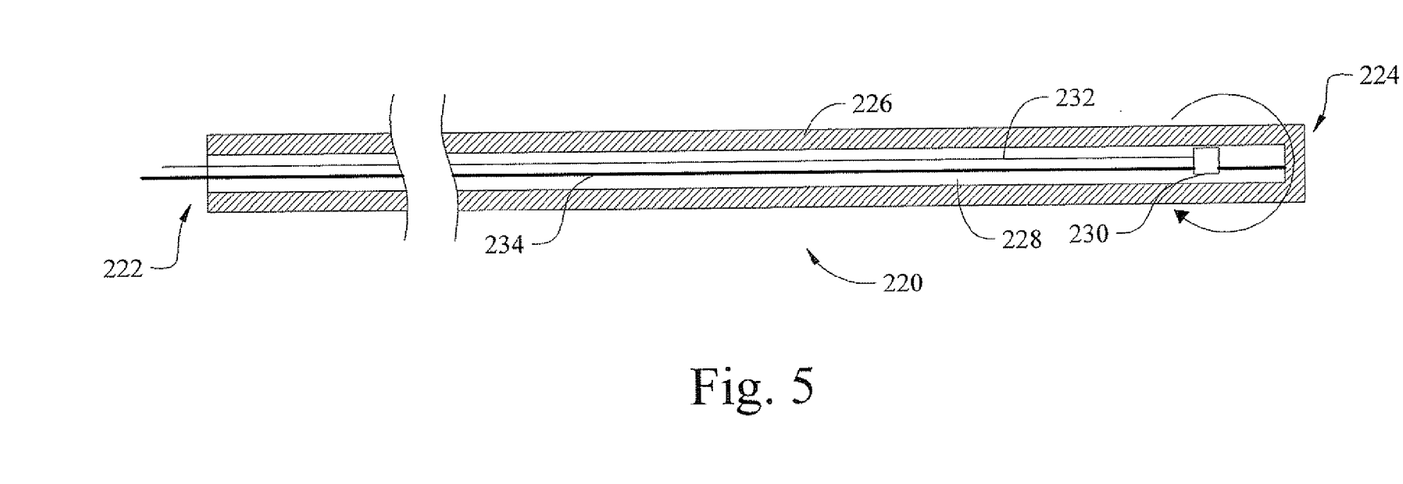
FIG. 5 is a longitudinal cross-sectional view of a third embodiment of a medical device constructed according to the principles of this invention.

A third embodiment of a medical device for navigation in a static magnetic field constructed in accordance with the principles of this invention is indicated generally as 220 in FIG. 5. As shown in FIG. 5, the device 220 is preferably an elongate device having a proximal end 222, a distal end 224, and comprising a generally tubular sidewall 226 with a lumen 228 extending therethrough. The distal end 224 of the medical device 220 preferably includes at least one element 230 for selectively creating a magnetic moment at the distal end of the medical device to orient the distal end of the medical device relative to a static magnetic field applied to the operating region in which the device 220 is being navigated by an external source magnet or magnets. The element 230 many be any of a variety of elements for selectively creating a magnetic moment, but in this preferred embodiment the element 230 comprises at least one electromagnetic coil, and more preferably at least three mutually perpendicular coils. These coils can be arranged on a cubic substrate or simply embedded in the wall of the medical device. The coils can be powered via leads 232, which preferably comprise a pair of leads for separately powering each coil. The leads 232 can either extend through the lumen 228 as shown, extend through a separate lumen (not shown), or be embedded in the wall 226.

A flexible cable 234 preferably extends through the lumen 228, and is anchored adjacent the distal end 224 of the medical device 220. The cable 234 is preferably sufficiently flexible so as not to unduly interfere with the flexing and navigation of the medical device 220, but has sufficient torsional stiffness so that rotation of the cable 234 rotates the distal end 224 of the medical device. Thus in operation, the element 230 is energized via the leads 232 and turned out of the forbidden plane, and then the cable 234 can be turned to turn the distal end 224 of the medical device 220 in the desired direction. The operation of the element 30 can be controlled by computer. It is desirable to know the orientation of the element 30 prior to energizing its coils. This can be conveniently done by moving the distal end of the medical device, and using the coils comprising the element 230 to measure the static field B and thereby determine their orientation relative to the known orientation of the field B. Likewise the turning of cable 234 may also be computer-controlled, with or without the use of feedback-control methods.

Figure 6:
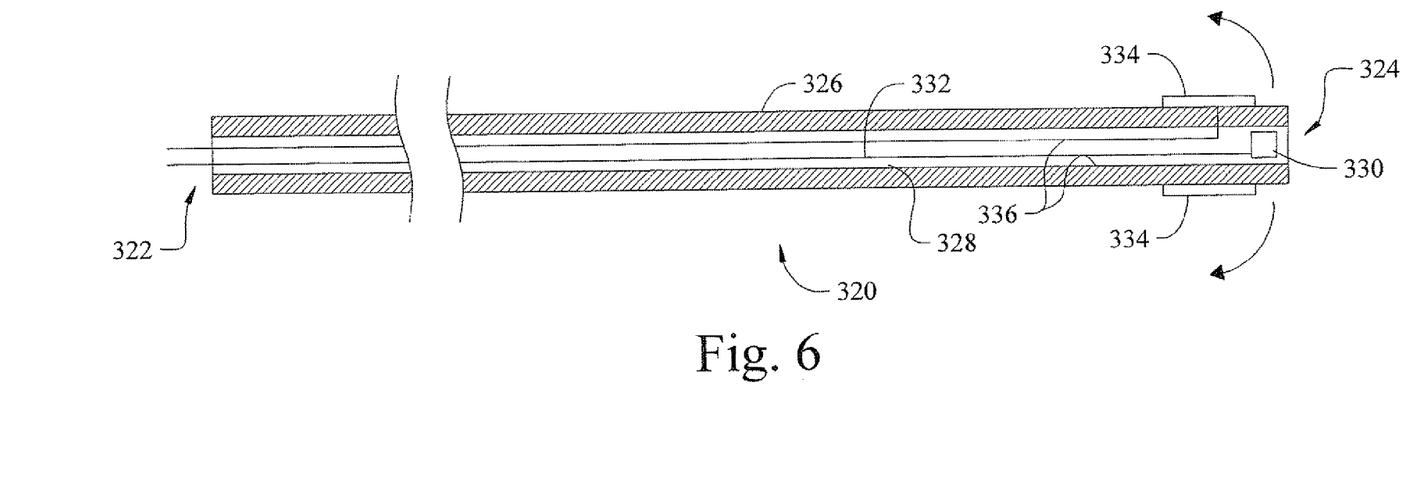
FIG. 6 is a longitudinal cross-sectional view of a fourth embodiment of a medical device constructed according to the principles of this invention.

A fourth embodiment of a medical device for navigation in a static magnetic field constructed in accordance with the principles of this invention is indicated generally as 320 in FIG. 6. As shown in FIG. 6, the device 320 is preferably an elongate device having a proximal end 322, a distal end 324, and comprising a generally tubular sidewall 326 with a lumen 328 extending therethrough. The distal end 324 of the medical device 320 preferably includes at least one element 330 for selectively creating a magnetic moment at the distal end of the medical device to orient the distal end of the medical device relative to a static magnetic field applied to the operating region in which the device 320 by an external source magnet or magnets. The element 330 many be any of a variety of elements for selectively creating a magnetic moment, but in this preferred embodiment the element 330 comprises at least one electromagnetic coil, and more preferably at least three mutually perpendicular coils. These coils can be arranged on a cubic substrate or simply embedded in the wall of the medical device. The coils can be powered via leads 332, which preferably comprise a pair of leads for separately powering each coil. The leads 332 can either extend through the lumen 328 as shown, extend through a separate lumen (not shown), or be embedded in the wall 326.

The distal end 324 of the medical device 320 preferably includes at least one bending element, such as electrostrictive bending elements 334, connected by leads 336. There are preferably a plurality of electrostrictive bending elements 334 and corresponding leads 336 disposed circumferentially around the distal end of the medical device 320. In the preferred embodiment there are at least four elements 334. These elements can be used individually or in groups to achieve the desired configuration. These elements can also be used in opposed pairs for example one element on one side of the device 320 constricting and one element on the other side of the device expanding to bend the device 320 in the desired direction.

In operation, the element 330 allows the distal end portion 324 of the medical device 20 to be turned out of the plane perpendicular to the field B, and then the electrostrictive elements 334 used to turn the distal end 324 in the desired direction. Alternatively, the distal end 324 of the medical device 320 can be bent using one or more of the elements 324, and then the element 330 can be operated to turn the distal end 324 in the desired direction. The operation of the elements 330 can be controlled by computer. Likewise the electrostrictive elements 334 can also be computer-controlled. It is desirable to know the orientation of the elements 330 prior to energizing their coils. This can be conveniently done by moving the distal end of the medical device, and using the coils comprising the element 330 to measure the static field B and thereby determine their orientation relative to the known orientation of the field B. An alternate method can be based on the use of suitable MR-visible markers in the device together with image processing.

Figure 7:
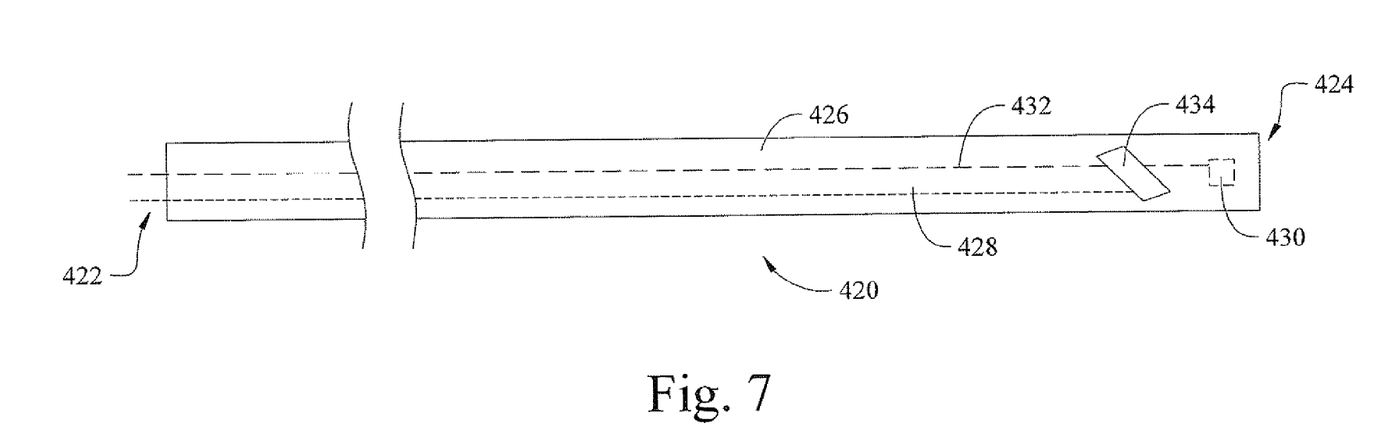
FIG. 7 is a side elevation view of a fifth embodiment of a medical device constructed according to the principles of this invention.

A fifth embodiment of a medical device for navigation in a static magnetic field constructed in accordance with the principles of this invention is indicated generally as 420 in FIG. 7. As shown in FIG. 7, the device 420 is preferably an elongate device having a proximal end 422, a distal end 424, and comprising a generally tubular sidewall 426 with a lumen 428 extending therethrough. The distal end 424 of the medical device 420 preferably includes at least one element 430 for selectively creating a magnetic moment at the distal end of the medical device to orient the distal end of the medical device relative to a static magnetic field applied to the operating region in which the device 420 is being navigated by an external source magnet or magnets. The element 430 many be any of a variety of elements for selectively creating a magnetic moment, but in this preferred embodiment the element 330 comprises at least one electromagnetic coil, and more preferably at least three mutually perpendicular coils. These coils can be arranged on a cubic substrate or simply embedded in the wall of the medical device. The coils can be powered via leads 332, which preferably comprise a pair of leads for separately powering each coil. The leads 432 can either extend through the lumen 428 as shown, extend through a separate lumen (not shown), or be embedded in the wall 426.

The distal end 424 of the medical device 420 preferably includes at least one bending element, such as electrostrictive twisting elements 434, connected by leads 436. There is preferably a plurality of electrostrictive torsional elements 434 and corresponding leads 436 disposed circumferentially around the distal end of the medical device 420. In the preferred embodiment there are at least four elements 434. These elements can also be used in opposed pairs for example one element on one side of the device 420 constricting and one element on the other side of the device expanding to bend the device 420 in the desired direction.

In operation, the element 430 allows the distal end portion 324 of the medical device 420 to be turned out of the plane perpendicular to the field B, and then the electrostrictive elements 434 used to turn the distal end 424 in the desired direction. Alternatively, the distal end 424 of the medical device 420 can be bent using one or more of the elements 424, and then the element 430 can be operated to turn the distal end 424 in the desired direction.

The operation of the elements 430 and that of the electrostrictive torsional elements 434 can be controlled by computer. It is desirable to know the orientation of the elements 430 prior to energizing their coils. This can be conveniently done by moving the distal end of the medical device, and using the coils comprising the element 430 to measure the static field B and thereby determine their orientation relative to the know orientation of the field B. An alternate method of orientation determination can be based on the use of suitable MR-visible markers in the device together with image processing.

Figure 8:
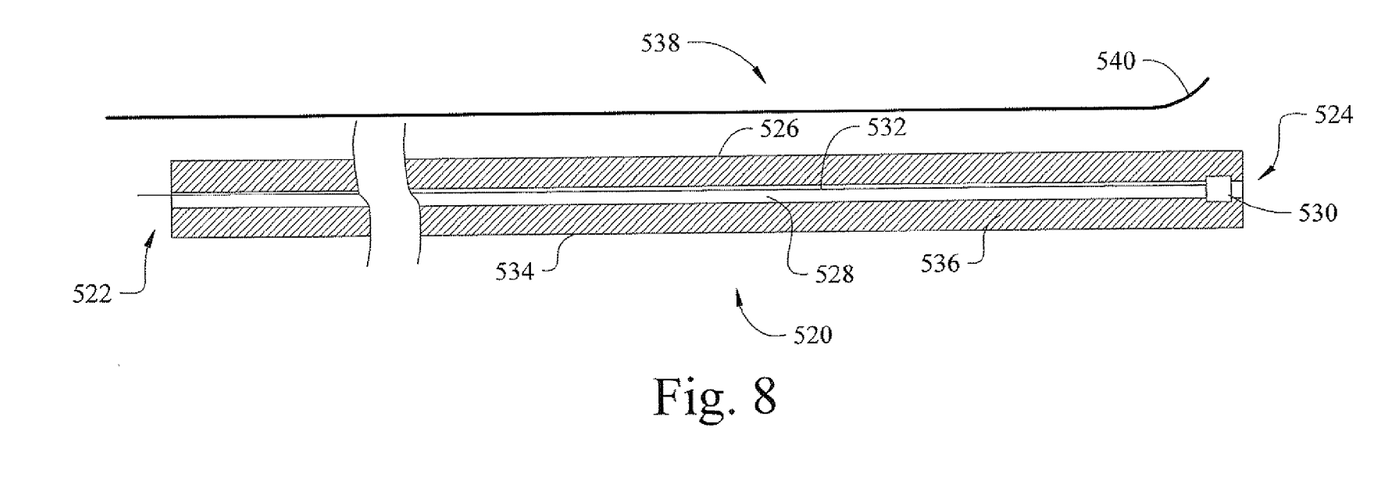
FIG. 8 is a longitudinal cross-sectional view of a sixth embodiment of a medical device constructed according to the principles of this invention.

A sixth embodiment of a medical device for navigation in a static magnetic field constructed in accordance with the principles of this invention is indicated generally as 520 in FIG. 8. As shown in FIG. 8, the device 520 is preferably an elongate device having a proximal end 522, a distal end 524, and comprising a generally tubular sidewall 526 with a lumen 528 extending therethrough. The distal end 524 of the medical device 520 preferably includes at least one element 530 for selectively creating a magnetic moment at the distal end of the medical device to orient the distal end of the medical device relative to a static magnetic field applied to the operating region in which the device 520 is being navigated by an external source magnet or magnets. The element 530 many be any of a variety of elements for selectively creating a magnetic moment, but in this preferred embodiment the element 530 comprises at least one electromagnetic coil, and more preferably at least three mutually perpendicular coils. These coils can be arranged on a cubic substrate or simply embedded in the wall of the medical device. The coils can be powered via leads 532, which preferably comprise a pair of leads for separately powering each coil. The leads 532 can either extend through the lumen 528 as shown, extend through a separate lumen (not shown), or be embedded in the wall 526.

The medical device 520 preferably includes at least one two sections 534 and 536 of differing flexibility. The more proximal section 534 is preferably stiffer than the more distal section 536. The medical device 520 is adapted for use with a stylette, such as stylette 538, which has a specially shaped, resilient distal tip 540. The stylette 538 is adapted to be inserted into the lumen 528, but because of the greater stiffness of the proximal end, as the shaped tip 540 of the stylette 538 passes through the proximal portion of the lumen, the shape remains unchanged. However, as the tip 540 of the stylette 538 passes through the distal portion of the lumen 528 in distal section 536, the distal portion of the medical device 520 bends to generally conform to the shaped tip 540.

In operation, the element 530 allows the distal end portion 524 of the medical device 520 to be turned out of the plane perpendicular to the field B, and then the stylette 538 can be used to turn the distal end 524 in the desired direction. Alternatively, the distal end 324 of the medical device 320 can be bent using the stylette 538, and then the element 530 can be operated to turn the distal end 524 in the desired direction.

The operation of the elements 530 can be controlled by computer. It is desirable to know the orientation of the elements 530 prior to energizing its coils. This can be conveniently done by moving the distal end of the medical device, and using the coils comprising the element 530 to measure the static field B and thereby determine their orientation relative to the know orientation of the field B. An alternate method for this purpose can combine image processing with the use of MR-visible markers.

Figure 9:
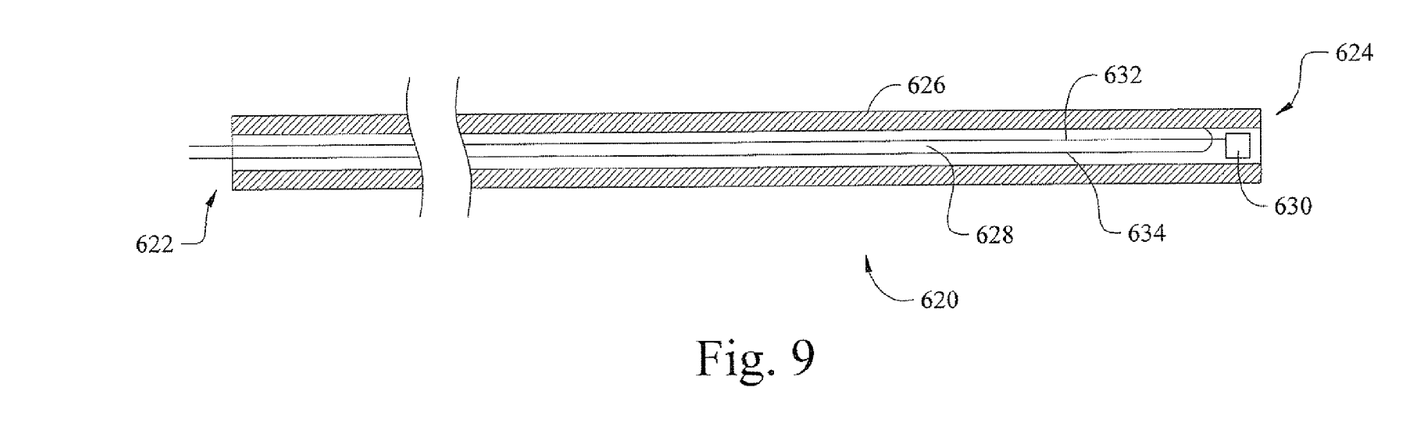
FIG. 9 is a longitudinal cross-sectional view of a seventh embodiment of a medical device constructed according to the principles of this invention.

A seventh embodiment of a medical device for navigation in a static magnetic field constructed in accordance with the principles of this invention is indicated generally as 620 in FIG. 9. As shown in FIG. 9, the device 620 is preferably an elongate device having a proximal end 622, a distal end 624, and comprising a generally tubular sidewall 626 with a lumen 628 extending therethrough. The distal end 624 of the medical device 620 preferably includes at least one element 630 for selectively creating a magnetic moment at the distal end of the medical device to orient the distal end of the medical device relative to a static magnetic field applied to the operating region in which the device is being navigated by an external source magnet or magnets. The element 630 may be any of a variety of elements for selectively creating a magnetic moment, but in this preferred embodiment the element 630 comprises at least one electromagnetic coil, and more preferably at least three mutually perpendicular coils. These coils can be arranged on a cubic substrate or simply embedded in the wall of the medical device. The coils can be powered via leads 632, which preferably comprise a pair of leads for separately powering each coil. The leads 632 can either extend through the lumen 628 as shown, extend through a separate lumen (not shown), or be embedded in the wall 626.

A expansible tube 634 (similar to a Bourdon tube pressure gauge) extends through the lumen 228, and is anchored adjacent the distal end 224 of the medical device 620. The tube has a wound configuration, and upon changes in the applied fluid pressure the wound portion 636 can wind or unwind, changing the shaped of distal end portion of the medical device 620.

Thus in operation, the element 630 is energized via the leads 632 and turned out of the forbidden plane, and then the expansible tube 634 is pressurized or depressurized to turn the distal end 624 of the medical device 620 in the desired direction. The operation of pressure turning the tip is that of a bending (pressure release) or unbending (pressure increase) of a Bourdon tube. Alternatively, the expansible tube 634 is pressurized or depressurized to turn the distal end 624 of the medical device 620 out of the "forbidden" plane, and then the element 630 is energized via the leads 632 to turn the device in the desired direction.

The operation of the element 630 can be controlled by computer. It is desirable to know the orientation of the element 630 prior to energizing its coils. This can be conveniently done by moving the distal end of the medical device, and using the coils comprising the element 630 to measure the static field B and thereby determine their orientation relative to the known orientation of the field B. In an alternate method of determination of orientation the use of MR-visible markers in the device can be combined with image processing.

Figure 10:
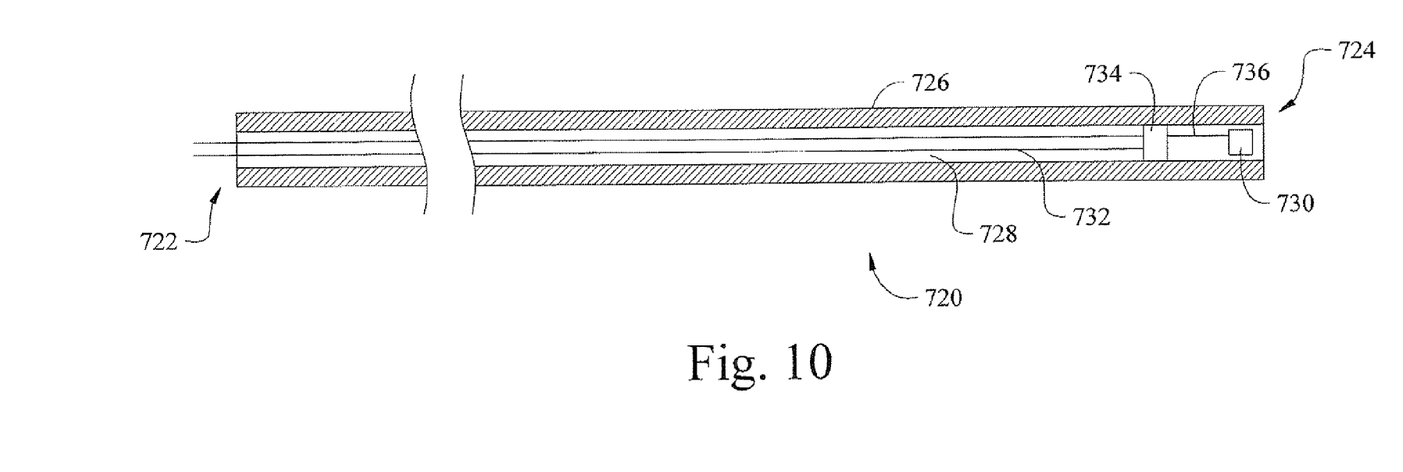
FIG. 10 is a longitudinal cross-sectional view of an eighth embodiment of a medical device constructed according to the principles of this invention.

An eighth embodiment of a medical device for navigation in a static magnetic field constructed in accordance with the principles of this invention is indicated generally as 720 in FIG. 10. As shown in FIG. 10, the device 720 is preferably an elongate device having a proximal end 722, a distal end 724, and comprising a generally tubular sidewall 726 with a lumen 728 extending therethrough. The distal end 724 of the medical device 720 preferably includes at least one element 730 for selectively creating a magnetic moment at the distal end of the medical device to orient the distal end of the medical device relative to a static magnetic field applied to the operating region in which the device 720 is being navigated by an external source magnet or magnets. The element 730 many be any of a variety of elements for selectively creating a magnetic moment, but in this preferred embodiment the element 730 comprises at least one electromagnetic coil, and more preferably at least three mutually perpendicular coils. These coils can be arranged on a cubic substrate or simply embedded in the wall of the medical device. The coils can be powered via a fiber optic lead 732, which conducts high energy light to a photovoltaic converter cell 734 to create electric power for the coils which is conducted to the coils via short lead 736. The use of a fiber optic lead 732 and photovoltaic cell 734 eliminates the need for long wire lead, which are sometimes subject to heating in the rf field of an MRI system. The fiber optic lead 732 can either extend through the lumen 728 as shown, extend through a separate lumen (not shown), or be embedded in the wall 726. This construction can be applied to any of the preceding embodiments one through seven.

There is preferably a photovoltaic cell for each electrically operated element, and a fiber optic line for each photovoltaic cell. Alternatively, a single fiber optic line can be provided that provides optic signals and optic power to control the distribution of light among a plurality of photovoltaic cells, or which controls the distribution of electric power among a plurality of electrical elements. For example the fiber optic can conduct information signals to operate an optical or electrical switch. Alternatively, a distribution device such as a filter can be used to distribute light based upon wavelength.

What is claimed is:

1. A method of turning a medical device with the assistance of an externally applied magnetic field, in a direction with a component in a plane perpendicular to the direction of the externally applied magnetic field, the method comprising:
applying a first torque to the distal end of the medical device by creating magnetic moment at a first point adjacent the distal end of the medical device; and
applying a second torque to the distal portion of the medical device at a second point spaced from the first point to turn the medical device in a direction with a component in a plane perpendicular to the direction of the externally applied magnetic field.

2. The method according to claim 1 wherein the magnetic moment is created by the application of an electric current to coils adjacent the distal end of the medical device.

3. The method according claim 1 wherein the second torque is applied by creating a second magnetic moment spaced from the point of application of magnet moment applying the first torque.

4. The method according to claim 1 wherein the second torque is applied by rotating the proximal end of the medical device.

5. The method according to claim 1 wherein the second torque is applied by rotating an element attached to the distal end of the medical device.

6. The method according to claim 5 wherein the element is flexible element extending through a lumen in the device, and having an end secured to the distal end of the medical device.

7. The method according to claim 1 wherein the second torque is applied by energizing at least one electrostrictive element the medical device.

8. The method according to claim 1 wherein the second torque is applied by inserting a shaped stylette into a lumen in the medical device.

9. The method according to claim 1 wherein the application of one of the first and second torques bends the medical device to orient the distal end portion of the medical device in a non-zero angle with respect to a plane perpendicular to the direction of the applied magnetic field.

10. A method of turning a medical device with the assistance of an externally applied magnetic field, in a direction with a component in a plane perpendicular to the direction of the externally applied magnetic field, the method comprising:
applying a first torque to the distal end of the medical device by creating magnetic moment at the distal end of the medical device;
applying a second torque to the distal portion of the medical device at a point spaced from the distal end of the medical device; and
changing the first torque as the second torque is applied to cause the medical device to move in a direction having a component in a plane perpendicular to the direction of the externally applied magnetic field.

11. The method according to claim 10 wherein the magnetic moment is created by the application of an electric current to coils adjacent the distal end of the medical device.

12. The method according to claim 11 wherein the second torque is applied by means of a magnetic moment at a location that is separated by a flexible length of device from the location of application of the first torque at the distal end of the device.

13. The method according to claim 11 wherein the second torque is applied by rotating the proximal end of the medical device.

14. The method according to claim 11 wherein the second torque is applied by rotating an element attached to the distal end of the medical device.

15. The method according to claim 11 wherein the second torque is applied by inserting a shaped element into the medical device.

16. The method of claim 15 where the shaped element has an effective stiffness that is larger in value than that of the distal portion of the medical device and smaller in value than that of the proximal portion of the medical device.

17. The method according to claim 10 wherein the second torque is applied by rotating the distal end of the medical device.

18. The method according to claim 10 wherein the second torque is applied by rotating an element attached to the distal end of the medical device.

19. A method of turning a medical device with the assistance of an externally applied magnetic field, in a direction with a component in a plane perpendicular to the direction of the externally applied magnetic field, the method comprising:
applying an electric current to at least one coil to create a magnetic moment at the distal end of the medical device to apply a first torque at the distal end of the medical device by creating magnetic moment at the distal end of the medical device; and applying a second torque to the distal portion of the medical device at a point spaced from the first torque.

20. The method of claim 19 wherein the second torque is applied by means of a magnetic moment at a location that is separated by a flexible length of device from the location of application of the first torque at the distal end of the device.

21. The method according to claim 19 wherein the second torque is applied by rotating the proximal end of the medical device.

22. The method according to claim 19 wherein the second torque is applied by rotating an element attached to the distal end of the medical device.

23. A method of turning a medical device with the assistance of an externally applied magnetic field, in a direction with a component in a plane perpendicular to the direction of the externally applied magnetic field, the method comprising:
   magnetically applying a first torque to the distal end of the medical device based upon a magnetic moment created in the distal end of the medical device and the applied magnetic field;
   mechanically applying a second torque to the distal portion of the medical device; and
   the combined first and second torques acting on the distal portion of the medical device to cause it to turn in a direction with a component in the plane perpendicular to the applied magnetic field.

24. A method of turning a medical device with the assistance of an externally applied magnetic field, in a direction with a component in a plane perpendicular to the direction of the externally applied magnetic field, the method comprising:
   magnetically applying a first torque to the distal end of the medical device based upon a magnetic moment created in the distal end of the medical device and the applied magnetic field;
   magnetically applying a second torque to the distal portion of the medical device at a second location separated from the location of application of the first torque by a flexible length of device, based upon a magnetic moment created at the second location and the applied magnetic field; and
   the combined first and second moments acting on the distal portion of the medical device to cause it to turn in a direction with a component in the plane perpendicular to the applied magnetic field.

25. A medical device for navigation in a static magnetic field, the device comprising a first element for selectively applying a first magnetic moment to the medical device, and a second element, spaced from the first for selectively applying a second magnetic moment.

26. The medical device according to claim 25 wherein the portion of the medical device between the first and second elements is sufficiently flexible to allow the medical device to bend.

27. A medical device for use in a magnetic field, the device having a proximal end and a distal end, at least one electrically powered coil element at the distal end for generating a magnetic moment sufficient to orient the distal end of the medical device relative to an externally applied magnetic field, a photovoltaic cell electrically connected to the electrically powered element, and a fiber optic lead extending from the proximal end to the photovoltaic cell to provide light to the photovoltaic cell to power the electrically powered coil element.

28. The medical device for use in a magnetic field according to claim 27 wherein there are a plurality of electrically powered elements and at least one photovoltaic cell for each electrically powered element.

\* \* \* \* \*